(12) United States Patent
Searle (10) Patent No.: US 8,562,913 B2
(45) Date of Patent: Oct. 22, 2013

(54) AIR FILTRATION AND PURIFICATION SYSTEM

(75) Inventor: Bruce R. Searle, Rainier, WA (US)

(73) Assignee: Acepower Logistics, Inc., Taipei (TW)

( * ) Notice: Subject to any disclaimer, the term of this patent is extended or adjusted under 35 U.S.C. 154(b) by 323 days.

(21) Appl. No.: 12/736,179

(22) PCT Filed: Mar. 27, 2008

(86) PCT No.: PCT/US2008/003996
§ 371 (c)(1),
(2), (4) Date: Sep. 17, 2010

(87) PCT Pub. No.: WO2009/120166
PCT Pub. Date: Oct. 1, 2009

(65) Prior Publication Data
US 2011/0006216 A1    Jan. 13, 2011

(51) Int. Cl.
*A62B 7/08*    (2006.01)
(52) U.S. Cl.
USPC .......................................... 422/122; 422/121
(58) Field of Classification Search
USPC .................................. 422/121, 122
See application file for complete search history.

(56) References Cited

U.S. PATENT DOCUMENTS

| 3,353,994 | A | 11/1967 | Welsh et al. | |
|---|---|---|---|---|
| 6,464,760 | B1 | 10/2002 | Sham | |
| 6,623,544 | B1 | 9/2003 | Kaura | |
| 2003/0183503 | A1* | 10/2003 | Fujii | 204/157.3 |
| 2006/0213157 | A1 | 9/2006 | Kalous et al. | |
| 2007/0041882 | A1 | 2/2007 | Roseberry et al. | |
| 2007/0253860 | A1* | 11/2007 | Schroder | 422/4 |

* cited by examiner

*Primary Examiner* — Walter D Griffin
*Assistant Examiner* — Christopher Vandeusen
(74) *Attorney, Agent, or Firm* — Brian J. Coyne (57) ABSTRACT

A system for filtering and purifying air within a closed environment. Air is drawn through a sequence of six filtration and purification stages, comprising, in order, an electrostatic prefilter to remove airborne impurities >=3 microns, an ultraviolet light source, a catalytic surface effective for breaking down hydrocarbons, a HEPA or other particulate filter for mechanically capturing airborne particles, a gas absorption filtration medium for removing volatile organic compounds and comprised primarily of activated charcoal, and an ionization module. The UV light is directed both upstream and downstream. The catalytic surface is semitransparent to UV light so that UV light strikes and kills microbes in the HEPA or other particulate filter medium.

15 Claims, 12 Drawing Sheets

AIR FILTRATION AND PURIFICATION SYSTEM

CROSS REFERENCE TO RELATED APPLICATIONS

This application claims the benefit of a provisional application by the same applicant for the same invention filed in the United States Patent and Trademark Office on Apr. 5, 2007, application No. 60/921,844.

STATEMENT REGARDING FEDERALLY APPROVED RESEARCH OR DEVELOPMENT

None.

BACKGROUND OF THE INVENTION

1. Field of the Invention

This invention relates to systems for filtering and purifying air drawn into a substantially enclosed environment, and particularly to such systems intended for improvement of indoor air quality in residential, commercial, medical and industrial environments by removing contaminants from the air.

2. General Background

Airborne contaminants are of various sizes and forms and include both inert and organic substances as well as biologically active contaminants such as pollens, bacteria and viruses. The spectrum of contaminants ranges from the angstrom size of individual molecules, as in the case of hydrocarbons and inert gases such as radon, to the particulates that range into micron size. Persons with respiratory issues who desire to breathe cleaner air normally seek relief from such contaminants by utilization or application of various filtration systems designed specifically to remove designated types of contaminants from the air that they breathe. It is commonly assumed that the removal of airborne particulates will alleviate upper respiratory tract irritation, whereas the true sources of such irritation may sometimes be hydrocarbons or other volatile organic compounds. Although health experts agree on the profound effect that these volatile airborne contaminants have upon the respiratory tract, their main focus has been on assaying the damage to health and finding the sources of the contaminants rather than finding solutions to the problem.

Although prior to my invention various types of mechanical and absorption filtering systems were known for removing particulate, hydrocarbon and other volatile organic compounds from air, it has not been so widely understood that these different technologies can be applied synergistically in a sequential process for filtering and purifying the air to obtain superior overall performance and efficiency as compared to applying these technologies separately or nonsequentially. By subjecting a flow of air to a sequence of mechanical and absorption filtering stages, my invention achieves effective and economical removal of the entire range of airborne contaminants, including particulates and volatile organic compounds, for residential, commercial, medical and industrial applications where cost and effectiveness are critical concerns.

SUMMARY OF THE INVENTION

The present invention provides six stages of filtering and purification of ambient air that is drawn into the system by a rotating fan through an air inlet end. An electrostatic prefilter at the first stage removes airborne matter 3 microns or larger. At the second stage, an ultraviolet light source irradiates incoming air as well as the downstream third and fourth stages. The third stage comprises a catalytic surface composed primarily of a titanium dioxide coating applied to a porous membrane together with various catalytic agents that are known to react with hydrocarbons at ambient air temperatures. The catalytic surface is semitransparent and porous thus allowing the UV radiation to penetrate through the catalytic surface and strike the fourth stage. At the fourth stage, a high efficiency air ("HEPA") or other particulate filter medium placed directly behind the catalytic surface mechanically captures airborne particulates from the incoming air and also receives UV radiation through the catalytic surface in order to eliminate the possibility of microbial infestation of the HEPA filter. Gas absorption occurs at the fifth stage, viz., a molecular filtration filter medium comprised primarily of activated charcoal breaks down and removes airborne hydrocarbons, including, but not limited to volatile organic compounds and any other unwanted constituents found in the air being filtered thorough the system. At the sixth stage, an ionization module releases negative ions into the air stream, which agglomerates any remaining airborne particles and enhances absorption of oxygen in human lungs. From the sixth stage, the air exits the system through an air outlet grill.

It is, therefore, an object of the invention to provide a system that subjects a flow of air to a sequence of mechanical and absorption filtering stages in order to efficiently and effectively filter and purify the air.

It is another object of the invention to provide such a system that includes at a first stage an electrostatic prefilter that will remove airborne impurities having major dimension of 3 microns or more from incoming ambient air.

It is a further object to provide such a system that includes at a second stage a source of ultraviolet light that is directed both upstream toward the incoming air as well as downstream toward a third stage of the system in order to destroy microbes.

Another object of the invention is to provide such a system that includes at a third stage a catalytic surface that is effective for breaking down hydrocarbons at ambient room temperature, which catalyst is semitransparent to ultraviolet light and porous to air flow.

A further object of the invention is to provide such a system that includes at a fourth stage a HEPA or other particulate filter medium for mechanically capturing airborne particulates.

Still another object of the invention is to provide such a system that includes at a fifth stage a molecular filtration medium effective in removing volatile organic compounds from air passing through said fifth stage.

Another object of the invention is to provide such a system that includes at a sixth stage an ionization module for releasing negative ions into the air stream.

A further object of the invention is to provide such a system wherein air is drawn through and past stages one through six in an ordered sequence corresponding to the numbering of said stages, whereby the filtration and purification stages are applied synergistically to obtain superior overall performance and efficiency as compared to applying these stages separately or nonsequentially.

BRIEF DESCRIPTION OF THE DRAWINGS

Except for FIG. 12, electric wiring has been omitted from the figures for the sake of clarity. Similar numerals denote similar component parts of the invention throughout the several views.

DETAILED DESCRIPTION OF A PREFERRED EMBODIMENT OF THE INVENTION

Figure 1:
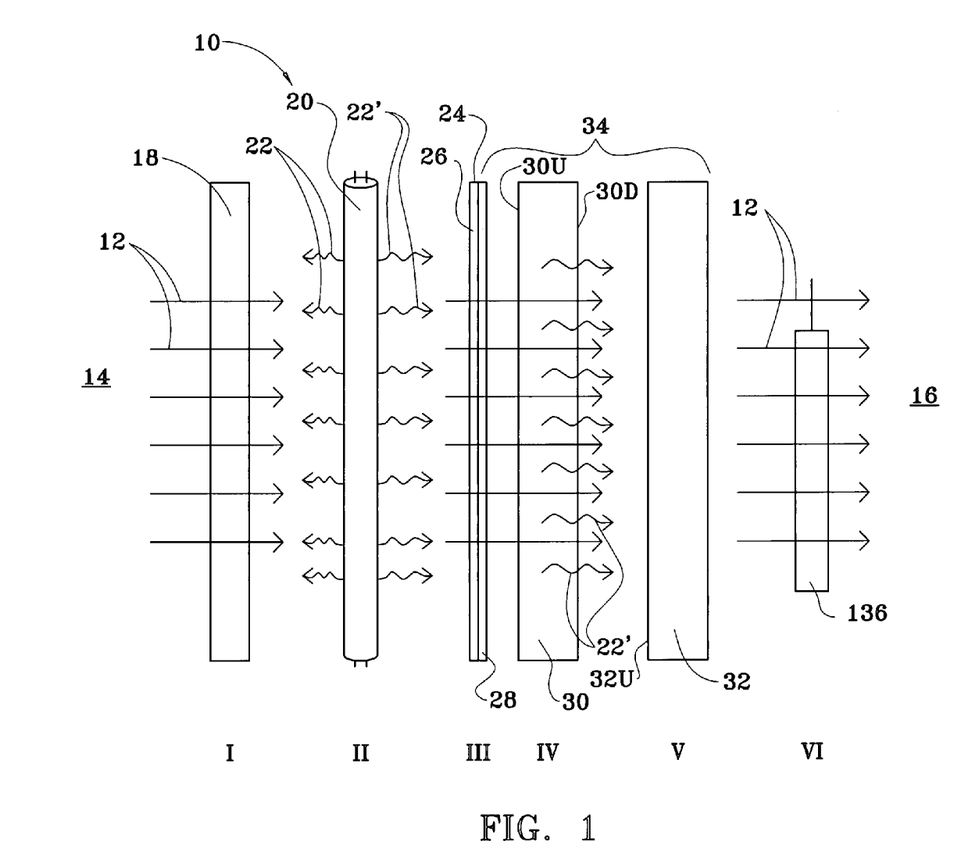
FIG. 1 is a schematic diagram of the six stages of filtering and purification, numbered I through VI, that ambient air undergoes as it passes through an exemplary embodiment of the invention, wherein the air stream is denoted by straight arrows and ultraviolet radiation is denoted by wavy arrows.

FIG. 1 schematically shows the six stages of an exemplary embodiment of the air filtration and purification system 10 of the present invention, labeled from left to right as stages I through VI. The straight arrows 12 denote flow of ambient air into and through the system from an air inlet end 14 to an air outlet end 16. Although the system 10 is a substantially closed system, except at the air inlet end 14 and the air outlet end 16, system enclosure details are omitted from FIG. 1 for the sake of clarity. The first stage comprises an electrostatic prefilter 18 that removes airborne matter three microns or larger.

The second stage, disposed downstream from the prefilter 18, comprises an ultraviolet light source assembly 20 that emits ultraviolet light in the upstream direction, denoted by undulating arrows 22, as well as in the downstream direction, denoted by undulating arrows 22'. When energized, the source 20 emits ultraviolet light, preferably having wavelength in the range 250 to 260 nm, and most preferably having wavelength 254 nm, for effective killing of microbes within the air stream 12 as well as microbes on and within the third and fourth stages of the system 10.

The third stage, disposed downstream from the ultraviolet source 20, comprises the combination 24 of a catalytic surface 26 applied to the upstream side of a porous membrane 28. The catalytic surface 26 includes primarily titanium dioxide, but may also include combinations of various catalytic agents known to react with hydrocarbons at ambient room temperatures. A type of reticulated foam or similar material that is resistant to breakdown by ultraviolet radiation is used to apply the titanium dioxide surface 26 to the porous membrane 28. The combination 24 of the catalytic surface 26 and the porous membrane 26 is semitransparent to ultraviolet light and is porous to air flow.

The fourth stage, disposed adjacent to and downstream from the combination 24, comprises a high efficiency air ("HEPA") or other particulate filtration filter medium 30 This stage captures airborne particulates from the incoming air and also receives UV radiation through the catalytic surface 24 and porous membrane 26, thereby eliminating the possibility of microbial infestation of the filter medium 30.

The fifth stage, disposed adjacent to and downstream from the particulate filtration filter medium 32, comprises a molecular filtration filter medium comprised primarily of activated charcoal together with various other materials. Those other materials preferably include, but are not limited to, potassium permanganate, activated alumina, synthetic zeolites and other materials able to absorb selective gases from the air, including but not limited to, volatile organic compounds and any unwanted constituents found in the air being filtered through the system 10. Preferably, a proprietary resin (not shown) is also added to the molecular filtration filter medium 32 to reduce the pore size of the membrane and thereby make it more selective for the smaller hydrocarbon molecules and less selective for absorption of the larger water molecules.

The sixth stage comprises an ionization module 136 that, when energized, neutralizes free radicals in the air, from whence air flows out the air outlet end 16 of the system 10. A suitable ionization module 136 is available from Wells Electronics, Taipei, Taiwan.

Figure 2:
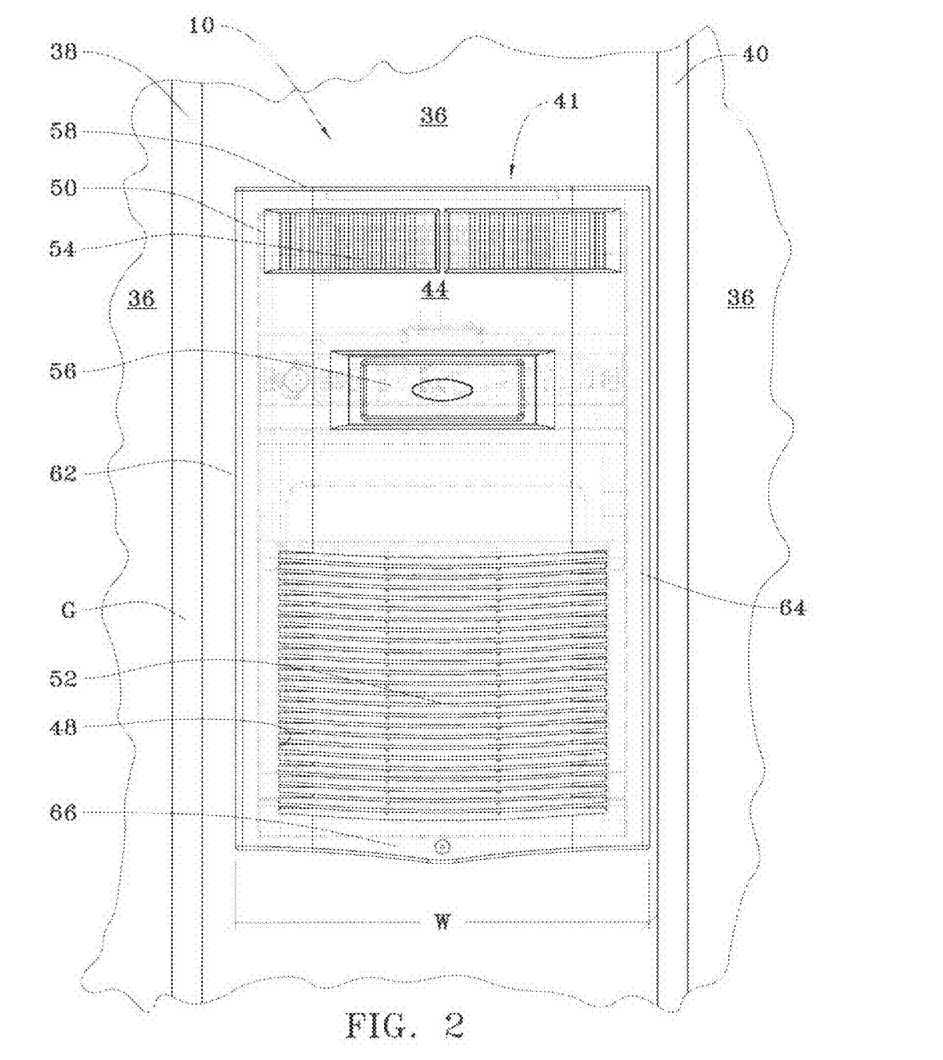
FIG. 2 is a front, elevational view of an exemplary embodiment of the invention installed in a wall between a pair of wall studs and with internal components of the system depicted in phantom outline.
Figure 3:
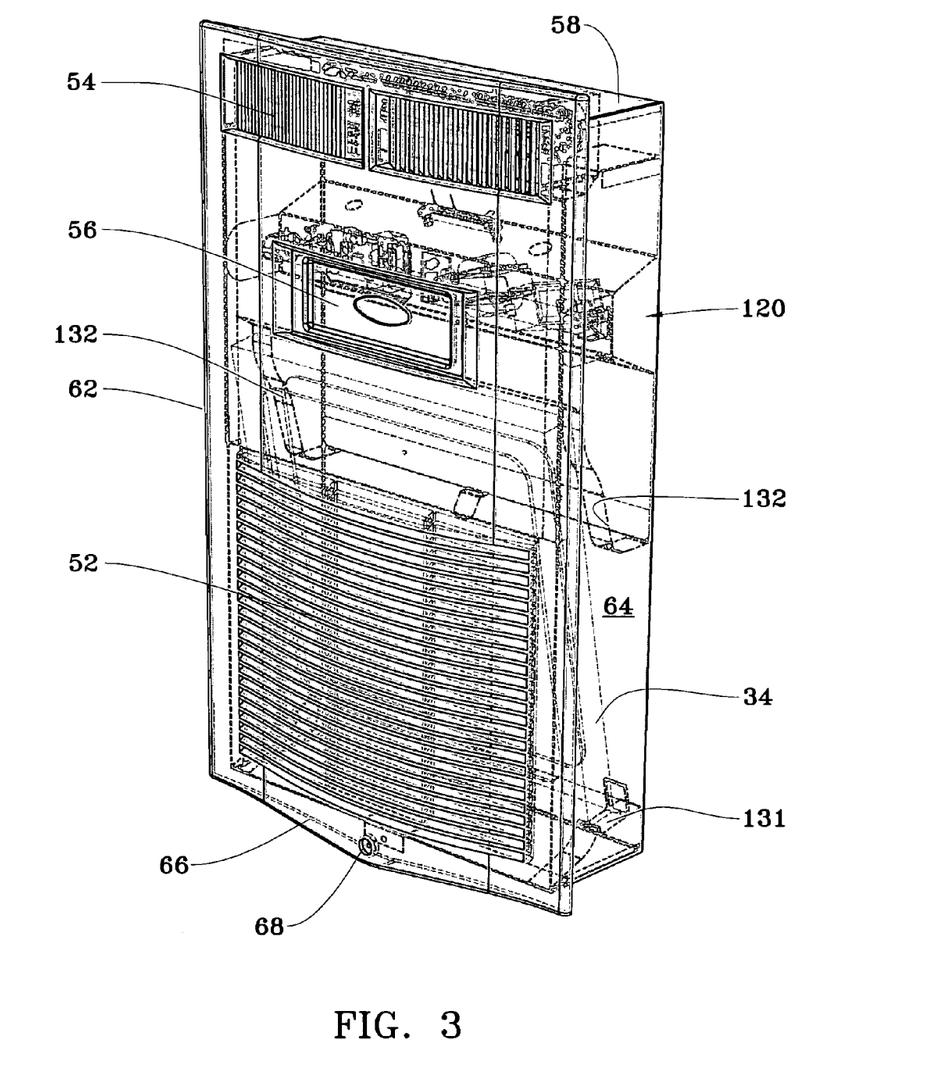
FIG. 3 is a front, perspective view thereof with internal components of the system depicted in phantom outline.
Figure 4:
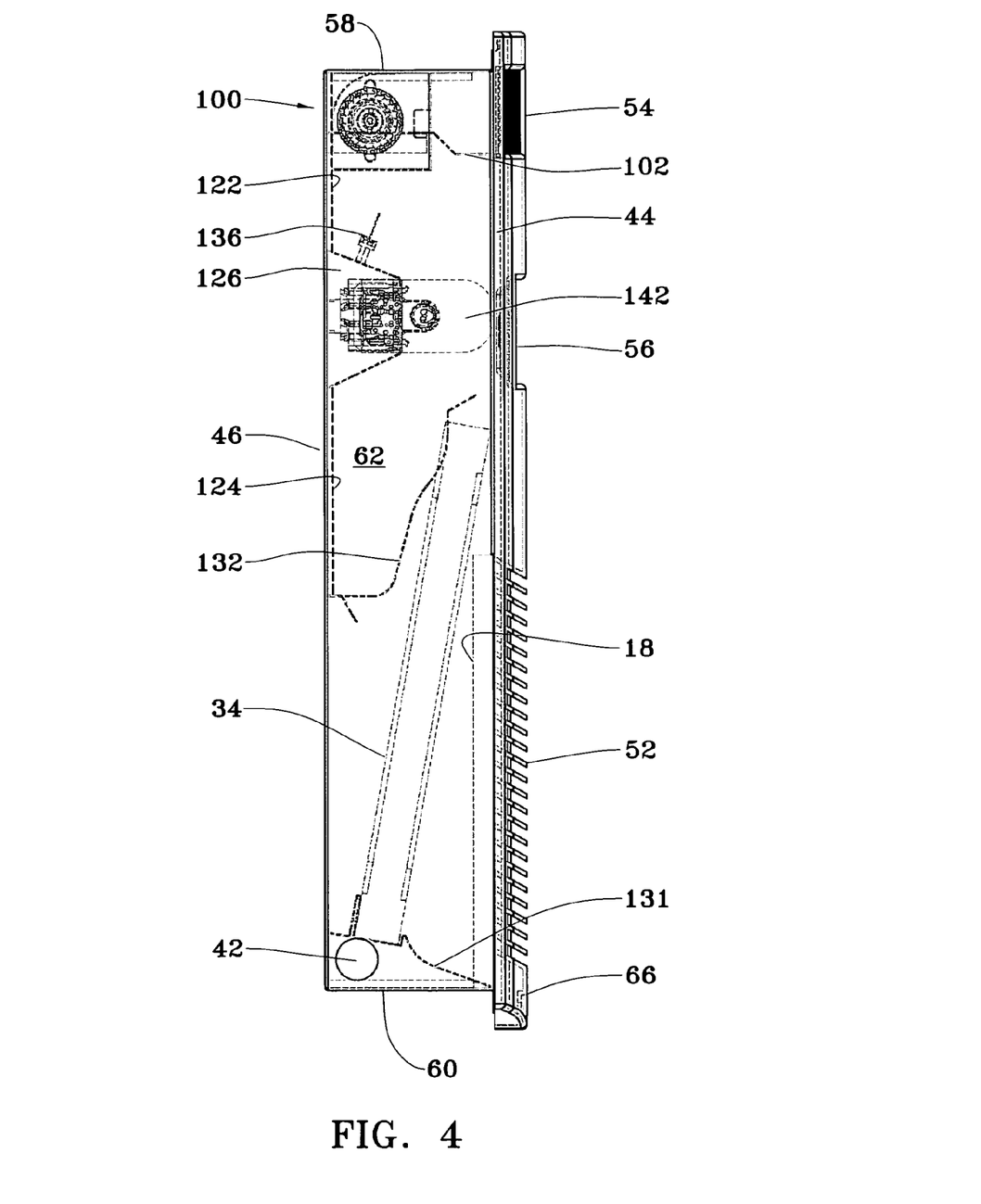
FIG. 4 is a left side elevational view thereof.
Figure 5:
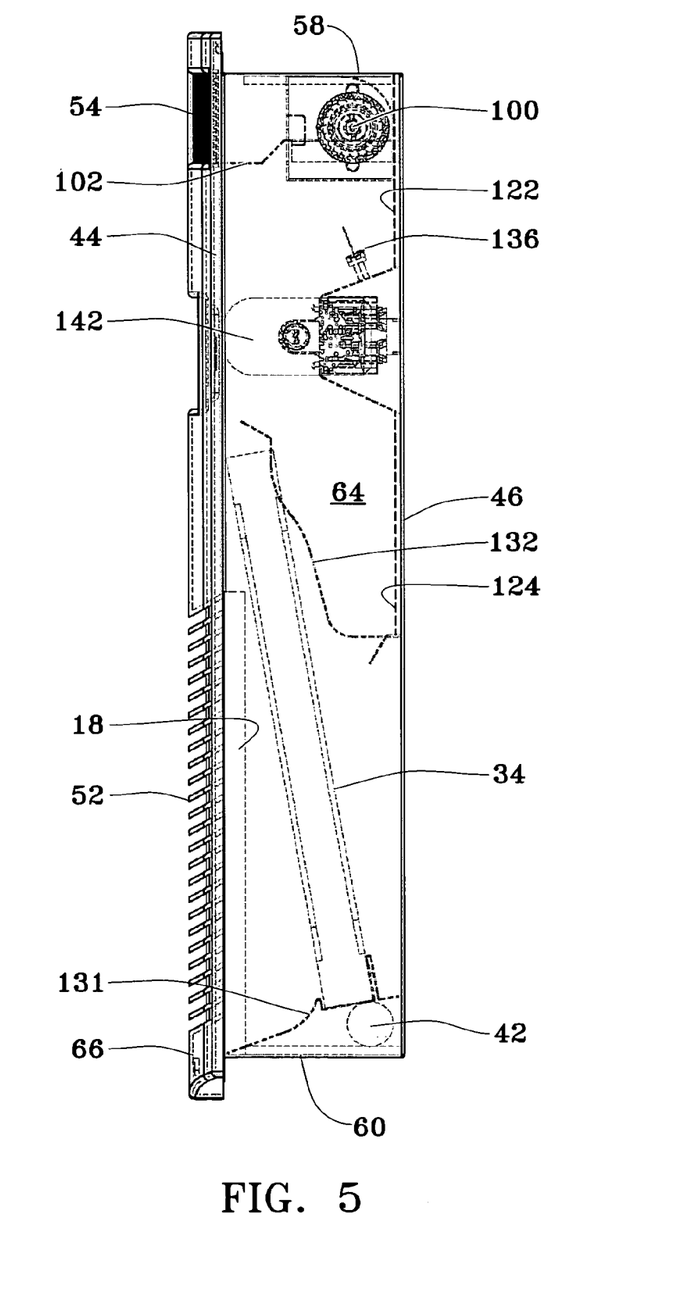
FIG. 5 is a right side elevational view thereof.
Figure 6:
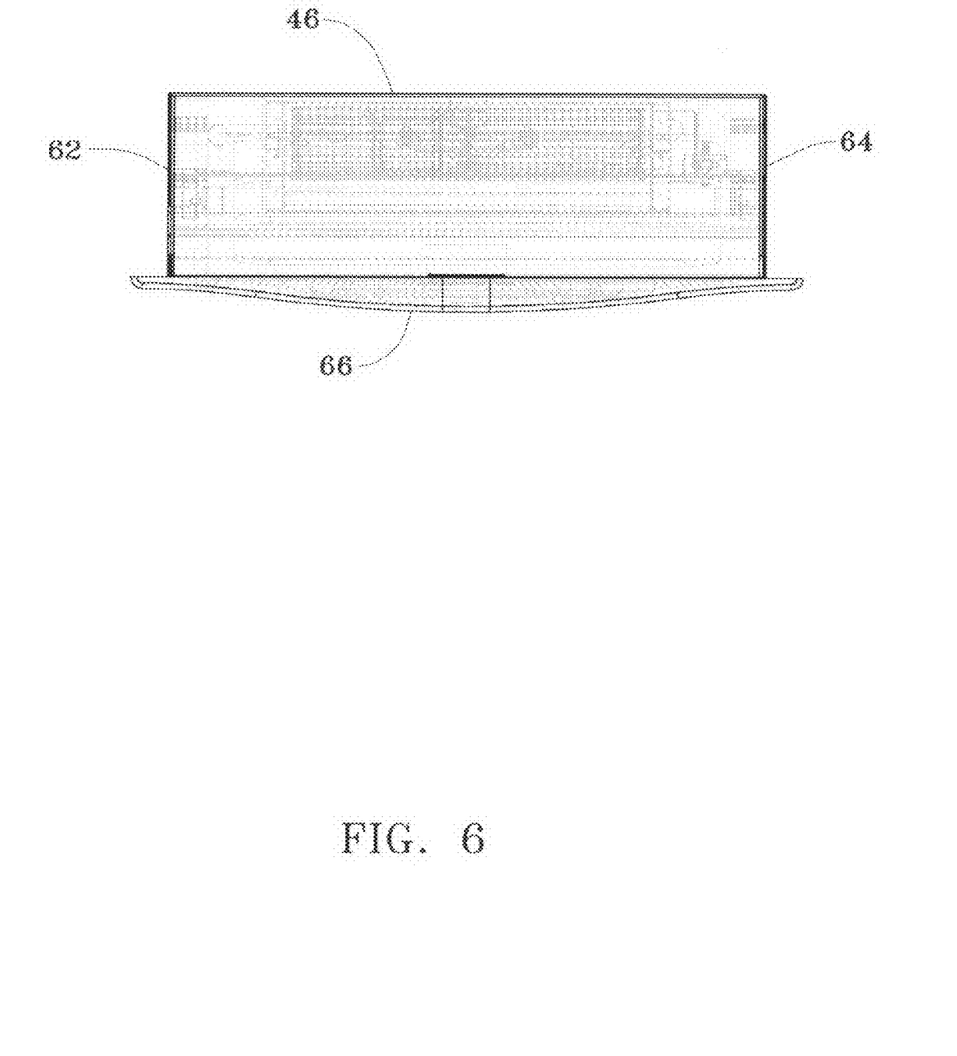
FIG. 6 is a bottom plan view thereof.
Figure 7:
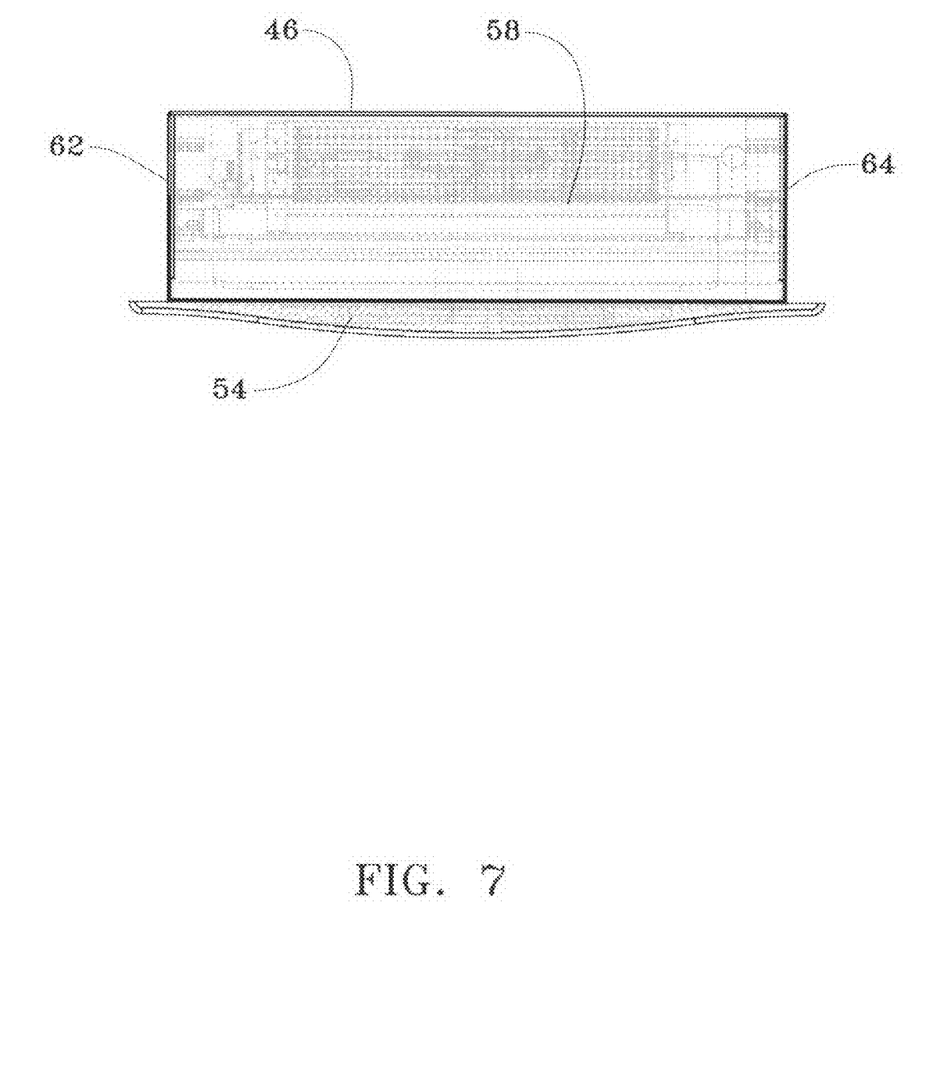
FIG. 7 is a top, plan view thereof.
Figure 8:
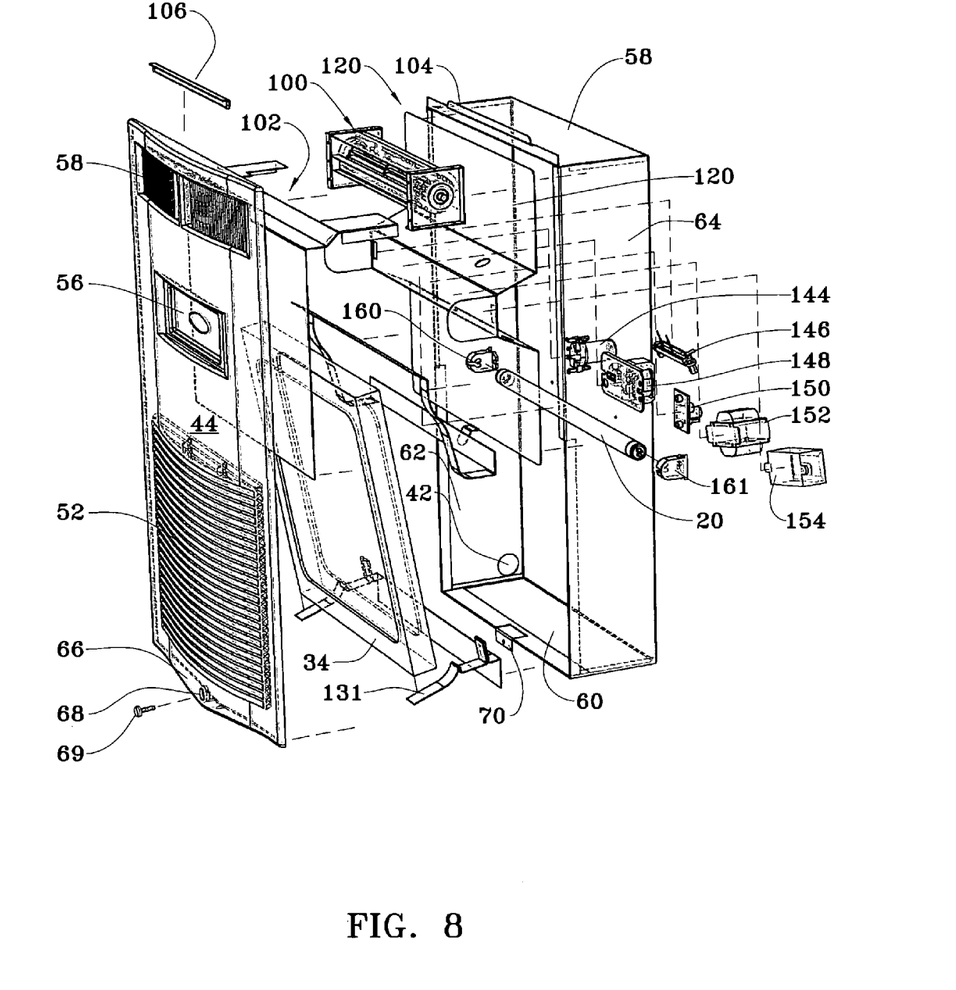
FIG. 8 is an exploded, right side perspective view thereof with wiring omitted for clarity.
Figure 12:
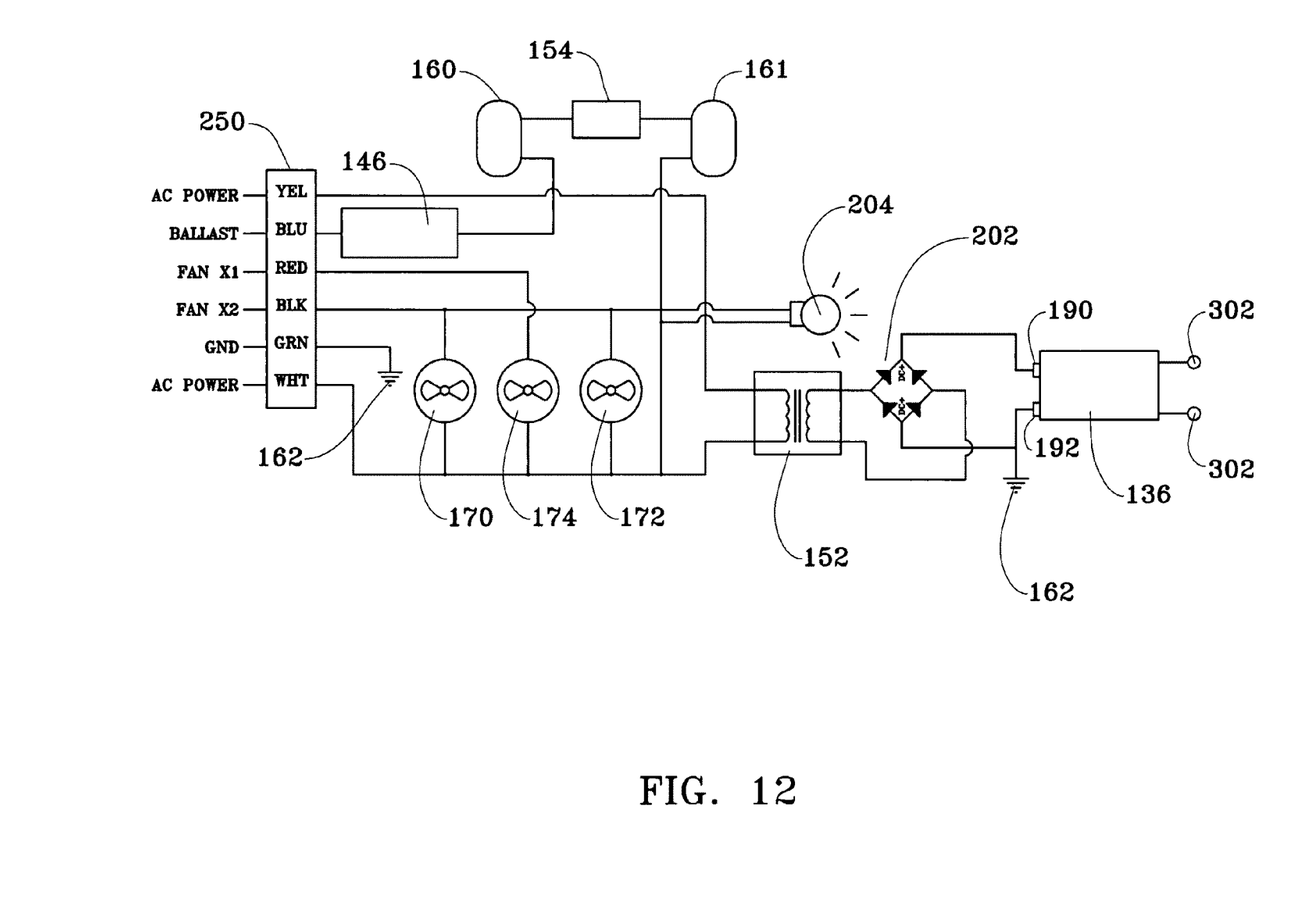
FIG. 12 is an electric wiring diagram for said embodiment.

Referring now to FIG. 2, a wall mountable version of the system 10 of the described exemplary embodiment of the present invention is depicted installed in a wall 36 between a left wall stud 38 and a right wall stud 40 by suitable fasteners (not shown). In order to fit between standard 16 inch on-center wall studs, for instance, the width W of the system must be somewhat less than 16 inches. Since, as best seen in FIG. 8, the system 10 has a power cord inlet port 42 on the lower left side thereof, the width W of the system preferably is chosen such that, when the system is placed flush against the right wall stud 40 a gap G remains between the left stud 38 and the system to accommodate a.c. power leads to be routed from the wall interior, through the power cord inlet port 42, and to an electric input terminal 250 of the system 10. As depicted in FIG. 12, the electric input leads are preferably and conveniently colored yellow ("YEL") and white ("WHT") for alternative current power leads, blue ("BLU") for a ballast power lead, red ("RED") and black ("BLK") for electric fan leads, and green ("GRN") for an electric ground lead.

Referring to FIGS. 3-8, except at an air inlet end 14 and an air outlet end 16, the system 10 is substantially enclosed by a housing, denoted generally by the numeral 41. The housing 41 includes a substantially flat, rectangular, vertical, front panel 44 spaced-apart in front-to-rear relation from a flat, rectangular, vertical rear panel 46 of substantially equal size. The front panel 44 has a rectangular air inlet opening 48 and a rectangular air outlet opening 50 that are covered, respectively, by an air inlet grill 52 and an air outlet grill 54. Disposed between the air inlet opening 48 and the air outlet opening 50 of the front panel 44 is a rectangular recess 56 that is adapted to receive and display a logo or emblem design. Top, bottom, left and right edges of the front panel 44 are joined to respective edges of the rear panel 46 by a rectangular top wall 58, bottom wall 60, left side wall 62 and right side wall 64. A lip extension 66 of the front panel 44 extends downward below the level of the bottom panel 60 and has a centrally-disposed aperture 68. An apertured bracket 70 depends from a front edge of the bottom panel 60, whereby a bottom portion of the front panel 44 can be attached to, and disattached from, the housing 41 by a suitable fastener such as a screw 69 inserted through the aperture 68. A top end of the front panel 44 is securable by a laterally-extended channel 106 to an upstanding lip 104 extension of a front portion of the top panel 58. To fit flush within a wall 36 of a room the housing 41 will ordinarily have a depth not exceeding 3.5 inches (8.9 cm).

A fan assembly 100 is mounted to an upper, interior portion of the housing 41 adjacent to the air outlet grill 54 by a mounting bracket 102 disposed immediately behind the air outlet grill 54. When the system 10 is electrically energized, a pilot light 204 lights up and the fan assembly 100 continuously draws room air into the system through the air inlet grill 52, through stages I through VI, and expels the filtered, purified air back out into the room through the air outlet grill 54. Preferably, as shown in FIG. 12, the fan assembly 100 includes three barrel fans 170, 172, 174 disposed laterally in tandem, each with its own electric motor, such that two fans 170, 172 are wired in parallel and will turn on and off together in response to manual activation of a wall-mounted a.c. power switch (not shown), and a third fan 174 is automatically turned on and off by a fan control 156 that includes an air inlet sensor for sensing impurities in the air stream 12 at the air inlet grill 52.

Figure 9:
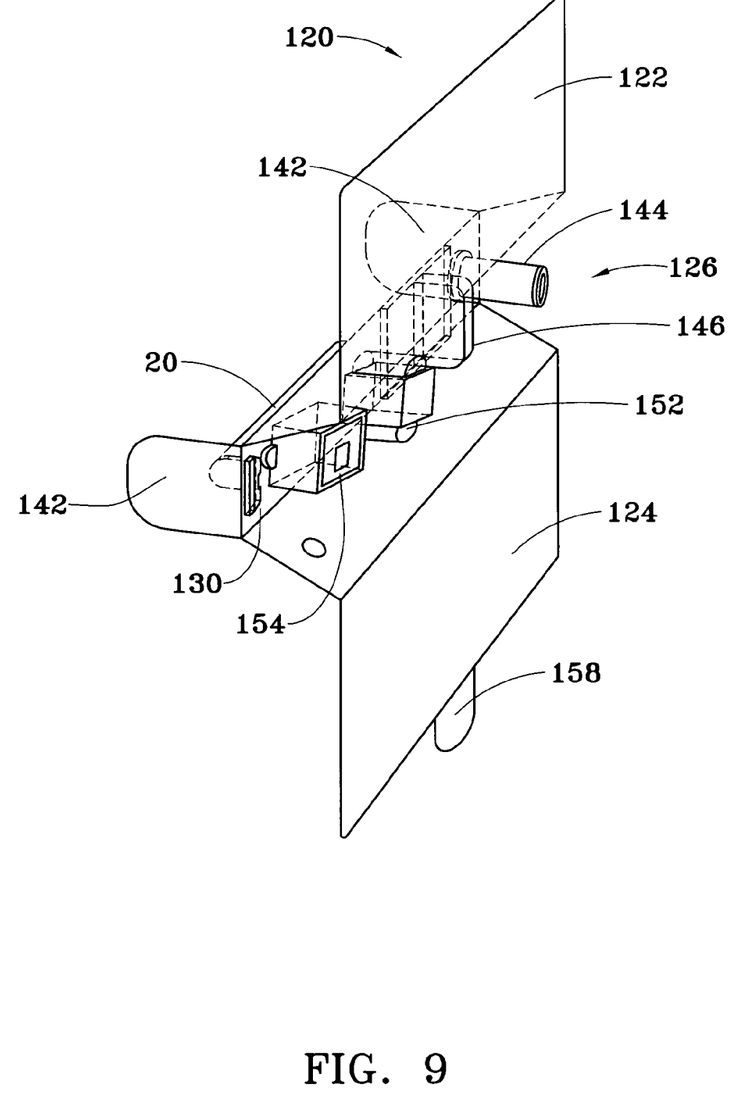
FIG. 9 is an enlarged, rear, perspective view of a baffle removed from the system showing the electronic components and the ultraviolet source mounted thereon.
Figure 10:
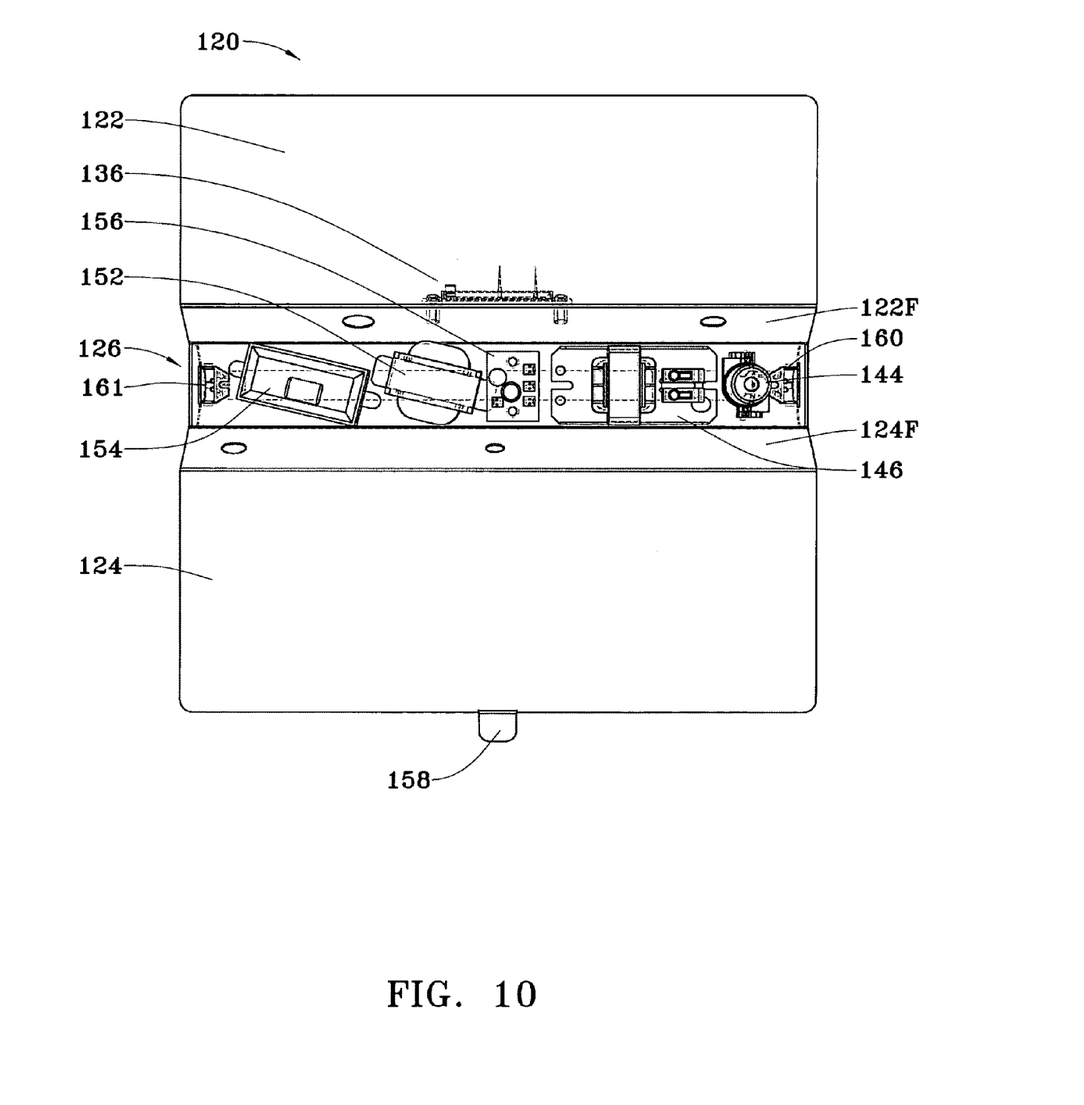
FIG. 10 is a further enlarged, front elevational view thereof.
Figure 11:
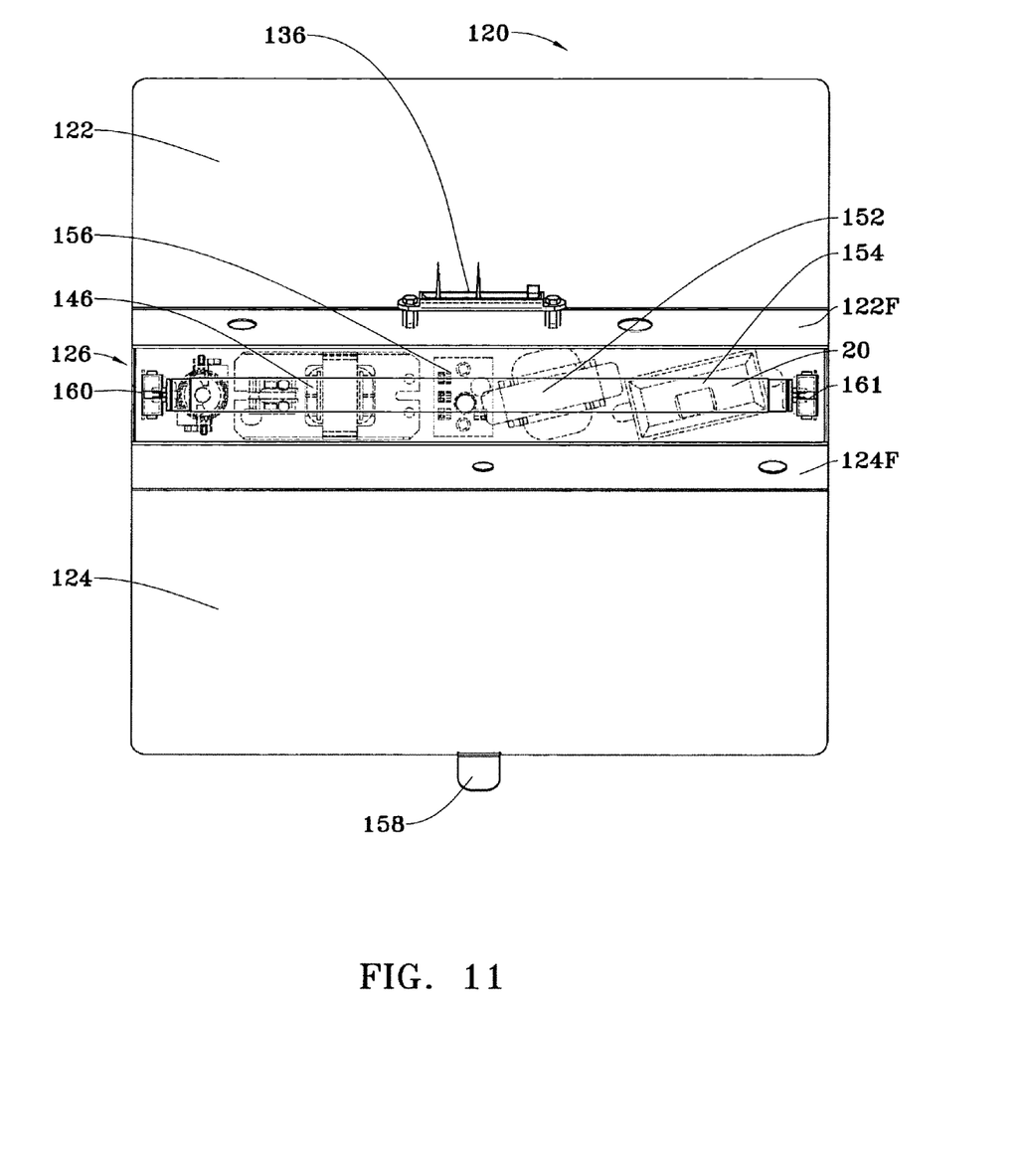
FIG. 11 is a further enlarged, rear elevational view thereof.

Disposed within an interior, upper portion of the housing 41 is a baffle 120 comprised of a flat, vertical upper baffle plate 122 and a flat, vertical lower baffle plate 124 joined by a forwardly-extended, central baffle section 126. The baffle 120 is attached to an interior surface of the rear panel 46 by fasteners (e.g., machine screws) and is removable when the front panel 44 is removed from the housing 41. The central baffle section 126 includes a flat, vertical electronics mounting board 130 that is suspended between the upper and lower baffle plates 122, 124 by upper and lower, canted flange panels 122F, 124F, respectively, whereby the central baffle section 126 has a partially trapezoidal, vertical cross-section that is open toward the front thereof, thereby defining an open channel space for mounting electronic components of the system to the mounting board 130. Mounted on a rear surface of the mounting board 130 are a high voltage generator 154 for energizing the ultraviolet source 20, a voltage transformer 152, a fan control 156, a light ballast 146, and a starter 144. The baffle 120 further includes a pair of laterally spaced-apart, vertical ears 142 that extend forward from the mounting board 130. The ears 142 each support a lamp holder 160 and each lamp holder electrically engages and supports an end of an ultraviolet lamp 166, whereby, when the ultraviolet lamp is electrically energized it can project ultraviolet radiation downward, forward and upward. An ionization module 136 is also mounted to a front surface of the mounting board 130, which when electrically energized ionizes the air as it moves past the front surface of the mounting board.

Stage 1 comprises a vertically-disposed, electrostatic membrane or prefilter 18 that is adjacent to an inside surface of the front panel 44 and behind the air inlet grill 52. The electrostatic membrane 18 is designed to trap and hold airborne particles of major dimension 3 microns or more and is removable for cleaning or replacement. A suitable electrostatic weave filter for this purpose is made by Permatron USA, Franklin Park, Ill.

Stages III, IV and V are preferably and conveniently combined into a single air filtration filter assembly 34, which includes a frame 34F that surrounds the peripheral edges of stages III, IV and V. The frame 34F holds the upwind surface 30U of the fourth stage adjacent to the downwind surface of the third stage, which is just the porous membrane 28, and holds the downwind surface 30D of the fourth stage adjacent to the upwind surface 32U of the fifth stage. An air filtration filter assembly 34 of this kind is manufactured by Sparks Technology, Inc. of Batavia, Ill. A pair of laterally-spaced apart, resilient filter assembly retaining clips 131 is attached to an upper surface of the bottom 60 into which a bottom edge portion of the frame 34F inserts. A pair of laterally-spaced apart, resilient guide strips 132 extend forwardly from the rear panel 46 in order to hold the air filtration filter assembly 34 within the housing 41 canted top forward and bottom rearward.

Referring to FIG. 12, which depicts an electrical circuit for the system 10, the primary coil of an electric transformer 152 is wired to the a.c. power input contacts of the terminal strip 250. Alternating current at a stepped up voltage in the secondary coil of the transformer 152 is rectified by a diode bridge 202 and applied to a first input terminal 190 of the ionization module 136 and thence drains to ground 162 through a second, output terminal 192 thereof. The ionization module 136 includes pointed extensions 302 that extend out into the air stream 12. A light ballast 146 is wired to the ballast terminal ("BLU") of the terminal strip 250 and to a first ultraviolet lamp holder 160, from whence current flows through the high voltage generator 154, through the second lamp holder 161, and through an a.c. power contact ("WHT") of the terminal strip, whereby an ultraviolet lamp 166 installed within the lamp holders 160, 161 will illuminate when the circuit is energized. A pilot lamp 204, wired in parallel to two of the electric fans 170, 172 and between an a.c. power input contact ("WHT") and a fan input contact ("BLK") of the terminal strip 250, lights whenever those two electric fans are energized. A third electric fan 174 that is wired to another fan input contact ("RED") of the terminal strip 250 and to an a.c. power input contact ("WHT") is energized whenever a switch within the fan control 150 closes in response to sensed impurities in the inlet air stream 12.

From the foregoing description it will be clear that the present invention may be embodied in other specific forms without departing from the spirit or essential characteristics thereof. For instance, the housing 41 and the component parts of the system 10 could be inverted with the air inlet opening 48, air inlet grill 52 and filter cartridge 34 disposed above the recess 56 and the air outlet opening 50, air outlet grill 54 and fan assembly 100 disposed below the recess. Alternatively, the housing 41 could be modified such that the air inlet opening 48 and air inlet grill 52 are eliminated, and room air is instead drawn into an electric heater installed within a room wall above, below, or adjacent to, and in communication with, the system 10, such that heated air is drawn from the heater into and through the system for filtration and purification. Thus, the presently disclosed embodiments are to be considered in all respects as illustrative and not restrictive, the scope of the invention being indicated by the appended claims, and not limited to the foregoing description.

I claim:

1. A system for filtering and purifying air drawn into a substantially enclosed environment, the system comprising:
   means for drawing in air that is to be filtered and purified into an air inlet end of the system, thence through an ordered sequence of air filtering and purifying stages of the system, and out an air outlet end of the system;
   a first stage, said first stage including an electrostatic pre-filter through which passes air that has been just been drawn into the system through the air inlet end, said pre-filter being adapted to attract and trap airborne particles;
   a second stage disposed downstream from the first stage, said second stage including a source of ultraviolet light;
   a third stage disposed downstream from the second stage and illuminated by ultraviolet light from said source, said third stage including a first catalytic surface comprising a catalyst effective for breaking down hydrocarbons at ambient room temperature, and said first catalytic surface being semitransparent to ultraviolet light and porous to air flow;

a fourth stage disposed downstream from, and adjacent to, the third stage, and illuminated by ultraviolet light that passes through the first catalytic means, said fourth stage including a HEPA or other particulate filter medium for mechanically capturing airborne particulates;

a fifth stage disposed downwind from the fourth stage, said fifth stage including a molecular filtration medium effective in removing volatile organic compounds from air passing through said fifth stage wherein the filtration medium of the fifth stage further includes a resin configured to reduce the pore size of the membrane and thereby make it more selective for the smaller hydrocarbon molecules and less selective for absorption of the larger water molecules; and a sixth stage disposed downwind from said fifth stage, said sixth stage including an ionization module;

and electric power means to energize the means for drawing in air and to energize all six stages;

whereby filtered, purified air is expelled from the air outlet end of the system.

2. The system of claim 1, wherein the first catalytic surface includes titanium dioxide attached to a porous membrane.

3. The system of claim 2, wherein titanium dioxide is adhered to the porous membrane of the first catalytic surface by reticulated foam that is semitransparent to ultraviolet radiation.

4. The system of claim 3, further comprising a housing that extends from the air inlet end to the air outlet end, an air inlet grill at the air inlet end and an air outlet grill at the air outlet end, and wherein the means for drawing in air that is to be filtered and purified includes an electric fan assembly mounted within the housing that, when energized, draws air in through the air inlet grill and through stages one through six, inclusive, and expels filtered, purified air from the system through the air outlet grill.

5. The system of claim 4, wherein the housing is adapted to fit snugly within the wall of a building and between wall studs.

6. The system of claim 5, wherein the ultraviolet emitted by the source of ultraviolet light is transmitted both upstream to the electrostatic prefilter in the first stage and downstream to said HEPA or other particulate filter medium in the fourth stage.

7. The system of claim 6, wherein the molecular filtration medium of the fifth stage includes activated charcoal.

8. The system of claim 7, wherein the filtration medium of the fifth stage further includes one or more of potassium permanganate, activated alumina, and synthetic zeolites.

9. The system of claim 8, wherein the first stage removes airborne matter having major dimension of three microns or more.

10. The system as in any of claims 1-8 or 9, wherein the source emits light of wavelength 250 to 260 nm.

11. The system of claim 10, wherein the source emits light of wavelength 254 nm.

12. An air filtration filter assembly for use in a system for filtering and purifying air drawn into a substantially enclosed environment through an air inlet end and discharged downwind through an air outlet end of said system, said system having a first stage that includes a prefilter and a second stage disposed downwind from the first stage that includes an ultraviolet source, said assembly comprising:

a third stage, said third stage including a first catalytic surface and an opposite downwind surface, said first catalytic surface comprising a catalyst effective for breaking down hydrocarbons at ambient room temperature and said first catalytic surface being semitransparent to ultraviolet light and porous to air flow;

a fourth stage, said fourth stage having an upwind surface and an opposite downwind surface, said upwind surface of said fourth stage being disposed adjacent to said downwind surface of said third stage, said fourth stage including a HEPA or other particulate filter medium for mechanically capturing airborne particulates; and a fifth stage disposed adjacent to the downwind surface of the fourth stage, said fifth stage including a molecular filtration medium effective in removing volatile organic compounds from air passing through said fifth stage wherein the filtration medium of the fifth stage further includes a resin configured to reduce the pore size of the membrane and thereby make it more selective for the smaller hydrocarbon molecules and less selective for absorption of the larger water molecules.

13. The assembly of claim 12, further comprising an air filtration filter assembly frame that surrounds and engages peripheral edge portions of said third, fourth and fifth stages, which frame holds said fourth stage adjacent to said third stage and said fourth stage adjacent to said fifth stage, whereby said third, fourth and fifth stages are combined to form a single unit insertable into said system.

14. The assembly of claim 13, wherein the molecular filtration medium of the fifth stage includes activated charcoal.

15. The assembly of claim 14, wherein the filtration medium of the fifth stage further includes one or more of potassium permanganate, activated alumina, and synthetic zeolites.

* * * * *